(12) United States Patent
Floyd et al.

(10) Patent No.: US 6,258,851 B1
(45) Date of Patent: Jul. 10, 2001

(54) METALLOPROTEINASE INHIBITORS

(75) Inventors: Christopher David Floyd; Sanjay Ratilal Patel; Mark Whittaker, all of Oxford (GB)

(73) Assignee: British Biotech Pharmaceuticals Limited (GB)

( * ) Notice: Subject to any disclaimer, the term of this patent is extended or adjusted under 35 U.S.C. 154(b) by 0 days.

(21) Appl. No.: 09/402,666

(22) PCT Filed: Mar. 31, 1998

(86) PCT No.: PCT/GB98/00958

§ 371 Date: Oct. 8, 1999

§ 102(e) Date: Oct. 8, 1999

(87) PCT Pub. No.: WO98/46563

PCT Pub. Date: Oct. 22, 1998

(30) Foreign Application Priority Data

Apr. 11, 1997 (GB) .................................................. 9707333

(51) Int. Cl.[7] ...................... A61K 31/165; C07C 233/64; C07C 323/39; C07C 323/41; C07C 311/18
(52) U.S. Cl. .......................... 514/618; 514/357; 514/602; 514/252.12; 514/256; 514/247; 514/292; 514/362; 514/363; 514/364; 514/393; 514/396; 514/424; 544/238; 544/335; 544/400; 546/84; 546/101; 546/336; 548/128; 548/131; 548/136; 548/314.7; 548/317.1; 548/335.1; 549/77; 549/462; 549/496; 564/90; 564/154
(58) Field of Search ..................... 564/90, 154; 546/336; 574/357, 602, 618

(56) References Cited

U.S. PATENT DOCUMENTS 5,902,791 * 5/1999 Beckett .................................. 514/19

FOREIGN PATENT DOCUMENTS

| WO 94/25434 | 11/1994 | (WO) . |
| WO 95/19961 | 7/1995 | (WO) . |
| WO 96/16027 | 5/1996 | (WO) . |
| WO 96/16931 | 6/1996 | (WO) . |

OTHER PUBLICATIONS

Hansson G and Ahnoff M. J. Chromatogr., A (1994), 666(1–2), 505–17.*
Brown FK et al. J. Med. Chem. 37(5), 674–688, 1994.*

* cited by examiner

*Primary Examiner*—Evelyn Mei Huang
(74) *Attorney, Agent, or Firm*—Banner & Witcoff, Ltd.

(57) ABSTRACT

Compounds of formula (I), wherein A, B, X, $R_1$, $R_2$, $R_3$, $R_4$, $R_5$, $R_6$ are as defined in the specification, are matrix metalloproteinase inhibitors.

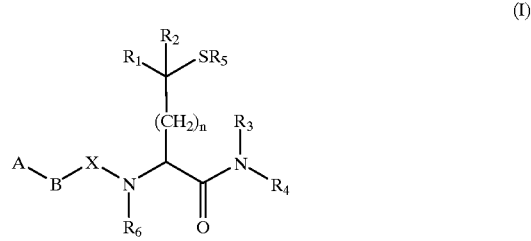

11 Claims, No Drawings

METALLOPROTEINASE INHIBITORS

This is the national phase of PTC/GB98/60985, filed Mar. 31, 1998.

The present invention relates to therapeutically active N-acyl alpha amino acid amides having a mercapto or acyl mercapto group in the amino acid side chain, to processes for their preparation, to pharmaceutical compositions containing them, and to the use of such compounds in medicine. In particular, the compounds are inhibitors of metalloproteinases involved in tissue degradation.

BACKGROUND TO THE INVENTION

The matrix metalloproteinases (MMPs) are a family of enzymes including interstitial collagenase, neutrophil collagenase, collagenase-3, 72 kDa gelatinase, 92 kDa gelatinase, stromelysin-1, stromelysin-2, stromelysin-3, matrilysin, macrophage metalloelastase, membrane-type metalloproteinase-1 and membrane-type metalloproteinase-2. These enzymes share a common zinc-containing catalytic domain and a pro-sequence which maintains latency. A wide range of cells and tissues can express MMPs in response to activation by inflammatory stimuli such as interleukin-1 or tumour necrosis factor-α (TNF-α). Different stimuli can induce overlapping yet distinct repertoires of MMPs and different cell types can respond to the same stimuli by expression of distinct combinations of MMPs. MMPs can attack the protein components of extracellular matrix such as collagens, vitronectin and elastin, and have recently been shown to process membrane proteins such as pro-TNF-α to release soluble TNF-α. MMPs are thought to play a central role in the pathology of inflammatory diseases such as rheumatoid arthritis as well as in the growth and metastasis of tumours.

Compounds which have the property of inhibiting the action of MMPs are thought to be potentially useful for the treatment or prophylaxis of conditions involving such tissue breakdown, for example rheumatoid arthritis, osteoarthritis, osteopenias such as osteoporosis, periodontitis, gingivitis, corneal epidermal or gastric ulceration, and tumour metastasis, invasion and growth. MMP inhibitors are also of potential value in the treatment of neuroinflammatory disorders, including those involving myelin degradation, for example multiple sclerosis, as well as in the management of angiogenesis dependent diseases, which include arthritic conditions and solid tumour growth as well as psoriasis, proliferative retinopathies, neovascular glaucoma, ocular tumours, angiofibromas and hemangiomas.

Two known classes of pseudopeptide or peptide mimetic MMP inhibitors have a hydroxamic acid group or a carboxylic group respectively as their zinc binding groups. Many such known MMPs may be represented by the structural formula (IA)

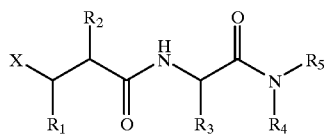

(IA)

in which X is the zinc binding hydroxamic acid (—CONHOH) or carboxylic acid (—COOH) group and the groups $R_1$ to $R_5$ are variable in accordance with the specific prior art disclosures of such compounds.

WO 96/16027 (Syntex/Agouron) discloses a class of MMP inhibitor compounds which can be represented by formula (IA) above. The principal structural characterising feature of the compounds disclosed in WO 96/16027 is the group $R_2$ which is defined in the publication as being a group $R^2$—X— wherein X is —$(CH_2)_m$—Y—$(CH_2)_n$, Y being O, S or a single bond, m and n being 0, 1, 2, 3 or 4 and m+n being 0, 1, 2, 3, or 4, and $R^2$ being (inter alia) aryl or heteroaryl, the latter terms including biaryl such as biphenyl and heteroaryl-aryl such as 4-pyridylphenyl.

Another known class of collagenase inhibitors is represented by those disclosed in EP-A-0574758 (Roche), EP-A-0684240 (Roche), and WO 95/33731 (Roche). In general, the compounds disclosed in those publications may be represented by the structural formula (IB):

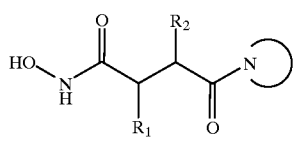

(IB)

in which $R_1$, $R_2$ and the N-containing ring are variable in accordance with the specific disclosures of the publications.

Foley et. al., Bioorg. Med. Chem Lett. 1996, 6:1905–1910 disclose MMP inhibitors which are C-terminal amido-, N-terminal acyl-dipeptides, wherein the zinc binding group is a mercapto group located in the side chain of the N-terminal amino acid.

BRIEF DESCRIPTION OF THE INVENTION

The present invention makes available a class of compounds which differ in structure from those disclosed by Foley et. al. principally in that they are derivatives of a single amino acid rather than a dipeptide, but also in other respects, for example the identity of the N-acyl group. Despite these structural modification relative to Foley et. al., compounds of the invention have been found to retain MMP inhibitory activity.

DETAILED DESCRIPTION OF THE INVENTION

According to the present invention, there is provided a compound of formula (I):

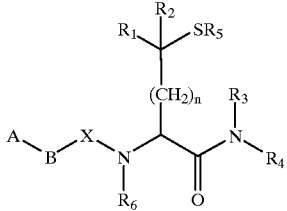

(I)

wherein:

n is 0 or 1;

A represents an optionally substituted phenyl or heteroaryl group;

B represents a divalent 1,4-phenylene moiety or a divalent $C_1$–$C_4$ alkylene or $C_2$–$C_4$ alkenylene or $C_2$–$C_4$ alkynylene moiety;

x represents —C(=O)— or —S(=O)$_2$—, $R_1$ and $R_2$
  (i) independently represent
    hydrogen,
    a $C_1$–$C_6$ alkyl group, or
    a group D-($C_1$–$C_6$ alkyl)- wherein D represents a 5- or 6-membered N-heterocyclic ring which (a) is attached via the N atom, (b) optionally contains N, O and/or S, SO or SO$_2$ as an additional ring member, (c) is substituted by oxo on one or both C atoms adjacent to the linking N atom and (d) is optionally benz-fused or optionally substituted on one or more other C atoms by $C_1$–$C_6$ alkyl, or oxo and/or on any additional N atoms by $C_1$–$C_6$ alkyl, phenyl or heteroaryl; or
  (ii) taken together with the carbon atom to which they are attached form a cycloalkyl or cycloalkenyl ring;

$R_3$ represents:
  (a) an optionally substituted cycloalkyl or cycloalkenyl ring or
  (b) a group —CHR$^x$R$^y$ wherein (i) R$^x$ and R$^y$ each independently represents an optionally substituted phenyl or heteroaryl group which may be linked covalently to each other by a bond or by a divalent $C_1$–$C_4$ alkyl or $C_2$–$C_4$ alkenyl bridge, or (ii) R$^x$ represents a group D-($C_1$–$C_6$ alkyl)- wherein D is as defined above in relation to $R_1$ and $R_2$, or is an optionally substituted phenyl or heteroaryl, group, and R$^y$ represents an optionally substituted phenyl or heteroaryl ring;
  (c) a group of formula -(Z'—O)$_w$-Z wherein Z' is straight or branched $C_1$–$C_6$ alkyl optionally interrupted by one or more non-adjacent S and/or N atoms, w is an integer >1, and no continuous linear sequence of atoms in the group $R_4$ is >12, or
  (d) hydrogen, $C_1$–$C_6$ alkyl, $C_1$–$C_4$ perfluoroalkyl, or a group D-($C_1$–$C_6$ alkyl)- wherein D is as defined above in relation to $R_1$ and $R_2$, or is hydroxy, $C_1$–$C_6$ alkoxy, $C_1$–$C_6$ alkylthio, acylamino, optionally substituted phenyl or heteroaryl, NH$_2$, or mono- or di-($C_1$–$C_6$ alkyl)amino;
  or $R_3$ and $R_4$ taken together represent a divalent chain of formula —C(R$^a$)(R$^b$)-A$^1$-Alk- wherein R$^a$ and R$^b$ are independently hydrogen or $C_1$–$C_6$ alkyl, A$^1$ is a bond, —O—, —S—, —S—S—, —NH— or —NR$^a$— wherein R$^a$ is $C_1$–$C_6$ alkyl, and Alk is a divalent $C_1$–$C_4$ alkylene moiety;

$R_4$ represents hydrogen or a $C_1$–$C_6$ alkyl group;

$R_5$ represents hydrogen or acyl; and $R_6$ represents hydrogen, a $C_1$–$C_6$ alkyl group, or a group D-($C_1$–$C_6$ alkyl)- wherein wherein D is as defined above in relation to $R_1$ and $R_2$;

or a salt, hydrate or solvate thereof.

As used herein, the term "cycloalkyl" means a saturated alicyclic moiety having from 3–8 carbon atoms and includes, for example, cyclohexyl, cyclooctyl, cycloheptyl, cyclopentyl, cyclobutyl and cyclopropyl.

As used herein the term "cycloalkenyl" means an unsaturated alicyclic moiety having from 4–8 carbon atoms and includes, for example, cyclohexenyl, cyclooctenyl, cycloheptenyl, cyclopentenyl, and cyclobutenyl. In the case of cycloalkenyl rings of from 5–8 carbon atoms, the ring may contain more than one double bond.

As used herein, the term "acyl" means a group $R_{20}$C(O)— where $R_{20}$ is $C_1$–$C_6$ alkyl, $C_2$–$C_6$ alkenyl, cycloalkyl, phenyl, heterocyclyt, phenyl($C_1$–$C_6$)alkyl, heterocyclyl ($C_1$–$C_6$)alkyl, cycloalkyl($C_1$–$C_6$ alkyl), phenyl($C_2$–$C_6$ alkenyl), heterocyclyl($C_2$–$C_6$ alkenyl), cycloalkyl($C_2$–$C_6$ alkenyl), any of which $R_{20}$ groups may be substituted.

The unqualified term "heterocyclyl" or "heterocyclic" as used herein means a 5–7 membered aromatic or non-aromatic heterocyclic ring containing one or more heteroatoms selected from S, N and O, and optionally fused to a carbocyclic or second heterocyclic ring. Specific examples of such groups include pyrrolyl, furyl, thienyl, imidazolyl, oxazolyl, thiazolyl, thiadiazolyl, pyrazolyl, pyridinyl, pyrrolidinyl, pyrimidinyl, morpholinyl, piperazinyl, indolyl, and benzimidazolyl.

The term "heteroaryl" as used herein means an aromatic 5 or 6 membered monocyclic aromatic heterocyclic group. Specific examples of the latter include thienyl, furyl, pyrrotyl, imidazolyl, thiazolyl, pyrazolyl, isoxazolyl, isothiazolyl, trizolyl, thiadiazolyl, oxadiazolyl, pyridinyl, pyridazinyl, pyrimidinyl, pyrazinyl and triazinyl.

An "optionally substituted phenyl or heteroaryl group" is a phenyl or heteroaryl group which is either unsubstituted or is substituted, and the term "substituted" means substituted with 1, 2, 3 or 4 compatible substituents selected from $C_1$–$C_8$ alkyl, $C_2$–$C_8$ alkenyl, $C_2$–$C_8$ alkynyl, $C_1$–$C_8$ alkoxy, $C_1$–$C_6$ alkoxy($C_1$–$C_6$ alkoxy), hydroxy, mercapto, $C_1$–$C_8$ alkylthio, $C_1$–$C_6$ alkylthio$C_1$–$C_6$ alkylthio, amino, halo (including fluoro, chloro, bromo and iodo), trifluoromethyl, nitro, CN, —COOH, —CONH$_2$, —COOR$^A$, —NHCOR$^A$, —NHCO$_2$R$^A$, —CONHR$^A$, or —CONR$^A$R$^B$ wherein R$^A$ and R$^B$ are each independently a $C_1$–$C_6$ alkyl, or benzyl group.

The term "protected" when used in relation to an amino, hydroxy, mercapto, or carboxy group means a derivative of such a group which is substantially non-functional. Such groups are widely known, for example from the art of peptide synthesis, and are discussed in the widely used handbook by T. W. Greene and P. G. M. Wuts, Protective Groups in Organic Synthesis, 2nd Edition, Wiley, N.Y., 1991. For example, carboxyl groups may be esterified (for example as a $C_1$–$C_6$ alkyl ester), amino groups may be converted to amides (for example as a NHCOC$_1$–$C_6$ alkyl amide) or carbamates (for example as an NHC(=O)OC$_1$–$C_6$ alkyl or NHC(=O)OCH$_2$Ph carbamate), hydroxyl groups may be converted to ethers (for example an OC$_1$–$C_6$ alkyl or a O($C_1$–$C_6$ alkyl)phenyl ether) or esters (for example a OC(=O)$C_1$–$C_6$ alkyl ester) and thiol groups may be converted to thioethers (for example a tert-butyl or benzyl thioether) or thioesters (for example a —SC(=O)$C_1$–$C_6$ alkyl thioester).

Salts of the compounds of the invention include physiologically acceptable acid addition salts for example hydrochlorides, hydrobromides, sulphates, methane sulphonates, p-toluenesulphonates, phosphates, acetates, citrates, succinates, lactates, tartrates, fumarates and maleates. Salts may also be formed with bases, for example sodium, potassium, magnesium, and calcium salts.

There is at least one, and there may be two or more, chiral centre(s) in the compounds according to the invention because of the presence of asymmetric carbon atoms. The presence of these asymmetric carbon atoms gives rise to stereoisomers or a number of diastereomers with R or S stereochemistry at each chiral centre. General formula (I), and (unless specified otherwise) all other formulae in this specification are to be understood to include all such stereoisomers and mixtures (for example racemic mixtures) thereof.

The group A in the compounds of the invention represents an optionally substituted phenyl or heteroaryl group. Heteroaryl A groups may be bonded to the rest of the molecule (I) via a ring carbon atom in A or via a ring nitrogen atom in A.

When the group A is substituted in accordance with the definition of A in formula (I), preferably only one substituent in present. In 6 membered A groups, such as phenyl and pyridyl, the substituent is preferably in the 4-position of the ring relative to the bond connecting A to the rest of molecule (I). In 5 membered A groups, such as thienyl and furanyl, the substituent is preferably in the 3- or 4-position of the ring relative to the bond connecting A to the rest of molecule (I). A sole substituent in A may be any of those defined above for "substituted". Preferred such substituents include $C_1$–$C_6$ alkyl eg methyl, ethyl, n-propyl, n-butyl, n-pentyl and n-hexyl; trifluoromethyl; halo eg chloro; cyano (—CN); —OH; and —OR, wherein R is $C_1$–$C_6$ alkyl, $C_1$–$C_6$ alkoxy ($C_1$–$C_6$ alkyl), or benzyl.

In the compounds of the invention:

n may be 0 or 1;

Group A may, for example, be phenyl, 4-chlorophenyl, 4-ethylphenyl, 4-n-hexylphenyl, 4-n-octyloxyphenyl; or pyridin-4-yl;

Group B may, for example, be 1,4-phenylene, —$CH_2$—, —$CH_2CH_2$—, —$CH_2CH_2CH_2$—, —$CH_2(CH_2)_2CH_2$—, —CH=$CH_2$—, —CH=$CH_2CH_2$—, —$CH_2$CH=$CH_2$—, —C≡C—, —$CH_2$C≡$CCH_2$—, —$CH_2$C57 C—, or —C≡$CCH_2$—;

Groups $R_1$ and $R_2$ may independently be, for example, hydrogen; a $C_1$–$C_6$ alkyl group for example methyl, ethyl, n- or iso-propyl, n-, sec- or tert-butyl, n-pentyl or n-hexyl; or a group D-$(CH_2)_m$—, wherein m is 1–6, for example 1, 2, 3 or 4, and D is, for example maleimido, succinimido, phthalimido, 1,2-dimethyl-3,5-dioxo-1,2,4-triazolidin-4-yl, 3,4,4-trimethyl-2,5-dioxo-1-imidazolidinyl, 2-methyl-3,5-dioxo-1,2,4-oxadiazol-4-yl, 3-methyl-2,4,5-trioxo-1-imidazolidinyl, 2,5-dioxo-3-phenyl-1-imidazolidinyl-2-oxo-1-pyrrolidinyl, 2,5-dioxo-1-pyrrolidinyl, 2,6-dioxopiperidinylnaphththalimido (ie 1,3-dihydro-1,3-dioxo-2H-benz[f]isoindol-2-yl), 1,3-dihydro-1-oxo-2H-benz[f]isoindol-2-yl, 1,3-dihydro-1,3-dioxo-2H-pyrrolo[3,4-b]quinolin-2-yl, 2,3-dihydro-1,3-dioxo-1H-benz[d,e]isoquinolin-2-yl group, or saccharinyl (1,1,3-trioxo-benz[3,4-d]isothiazol-2-yl);

Taken together with the carbon atom to which they are attached, groups $R_1$ and $R_2$ may form, for example, a cycloalkyl or cycloalkenyl ring, for example a cyclopropyl, cyclobutyl cyclopentyl, cyclohexyl, cyclohex-1,2-enyl, cyclohex-2,3-enyl, or cyclohex-3,4-enyl ring;

Group $R_3$ may for example be cyclopropyl, cyclobutyl, cyclopentyl, cyclohexyl cycloheptyl or cyclooctyl;

optionally substituted phenyl, napthyl, furanyl, thienyl, pyrrolinyl, tetrahydrofuranyl, imidazolyl, oxadiazolyl, thiazolyl, thiadiazolyl, pyridinyt, pyridinyl N-oxides, piperazinyl, indolyl, benzimidazolyl, benzotriazolyl, pyrazinyl, pyridazinyl, pyrimidinyl, dithianyl, benzo[b]thienyl, isoxazolyl or quinolinyl. Examples of particular $R_3$ groups of this type include phenyl, 2-methoxyphenyl, 3-methoxyphenyl, 4-methoxyphenyl, 3,4-dimethoxyphenyl, 2-fluorophenyl, 3-fluorophenyl, 4-fluorophenyl, 2-chlorophenyl, 3-chlorophenyl, 4-chlorophenyl, 3,4-dichlorophenyl, 3,5-dichlorophenyl, 2-bromophenyl, 3-bromophenyl, 4-bromophenyl, 2-iodophenyl, 3-iodophenyl, 4-iodophenyl, 2-methylphenyl, 3-methylphenyl, 4-methylphenyl, 3,4-dimethyl, 2-t-butylphenyl, 3-t-butylphenyl, 4-t-butylphenyl, 4-t-butyl-2,6-dimethylphenyl, 2-nitrophenyl, 3-nitrophenyl, 4-nitrophenyl, 2-cyanophenyl, 3-cyanophenyl, 4-cyanophenyl, 2-acetylphenyl, 3-acetylphenyl, 4-acetylphenyl, 2-methylsulphonylphenyl, 3-methylsulphonylphenyl, 4-methylsulphonylphenyl, 2-trifluoromethylphenyl, 3-trifluoromethylphenyl, 4-trifluoromethylphenyl, 3,5-ditrifluoro-methylphenyl, 2-aminophenyl, 3-aminophenyl, 4-aminophenyl, 2-N,N-dimethylaminophenyl, 3-N,N-dimethylaminophenyl, 4-N,N-dimethylaminophenyl, 2-hydroxyphenyl, 3-hydroxyphenyl, 4-hydroxyphenyl, 2-napthyl, furan-2-yl, thien-2-yl, pyrrol-2-yl, tetrahydrofuran-2-yl, imidazol-2-yl, thiazol-2-yl, 4-ethoxycarbonyl-methylthiazol-2-yl, 4-phenylthiazol-2-yl, 4,5-dimethylthiazol-2-yl, 5-bromothiazol-2-yl, 4-tert-butylthiazol-2-yl, benzothiazol-2-yl, 1,2,4-oxadiazol-5-yl, 3-methyl-1,2,4-oxadiazol-5-yl, 3-phenyl-1,2,4-oxadiazol-5-yl, 1,2,4-oxadiazol-3-yl, 1,3,4-oxadiazol-2-yl, 1,2,4-thiadiazol-5-yl, 3-phenyl-1,2,4-thiadiazol-5-yl, 1,3,4-thiadiazol-2-yl, 5-methyl-1,3,4-thiadiazol-2-yl, pyridin-2-yl, pyridin-3-yl, pyridin-4-yl, N-oxides of pyridin-2-yl pyridin-3-yl and pyridin-4-yl, piperazin-1-yl, indol-2-yl, benzimidazol-2-yl, benzotriazol-2-yl, pyrazin-2-yl, 1,2-pyridazin-3-yl, 1,3-pyrimidin-5-yl, 1,3-dithian-2-yl, benzo[b]thien-2-yl, isoxazol-5-yl, or quinolin-3-yl;

a group —CHR$^x$R$^y$ wherein R$^x$ and R$^y$ independently represent optionally substituted phenyl, thienyl, furyl, pyrrolyl, imidazolyl, thiazolyl, pyrazolyl, isoxazolyl, isothiazolyl, triazolyl, thiadiazolyl, oxadiazolyl, pyridinyl, pyridazinolyl, pyrimidinyl, piperazinyl or triazinyl. Examples of particular $R^x$ and $R^y$ include phenyl, 4-chlorophenyl and pyridinyl. Where $R^x$ and $R^y$ are linked covalently, an example of a group $R_4$ is 9-H-fluoren-9-yl;

a polyether chain possessing at least two non-adjacent oxygen atoms, for example 2-(2-methoxyethoxymethoxy)ethyl, 1,1-dimethyl-2-(2-methoxyethoxymethoxy)ethyl, 2-(2-ethoxyethoxymethoxy)ethyl, 2-(2-(2-methoxyethoxy)ethoxy)ethyl, 2-(2-(3-methoxypropoxymethoxy)ethyl, 3-(2-methoxyethoxymethoxy)propyl, 2,2-dimethyl-3-(2-methoxyethoxymethoxy)propyl, 2-(2-methoxyethoxy)ethyl, 3-(2-methoxyethoxy)-propyl, 2-methyl-2,2-di(2-methoxyethyl)propyl, 2-methyl-2,2-di(2-methoxyethyl)butyl, and 2-methyl-2,2-di(2-methoxymethyl)propyl;

hydrogen, methyl, ethyl, n- or iso-propyl, n-, sec- or tert-butyl, a group D-$(CH_2)_m$—as exemplified above for $R_1$ and $R_2$, hydroxyethyl, hydroxypropyl, 2,2-dimethyl-3-hydroxypropyl, hydroxybutyl, methoxyethyl, ethoxyethyl, methoxypropyl, 2,2-dimethyl-3-methoxypropyl, 2,2-dimethyl-3-ethoxypropyl, 2-ethylthioethyl, 2-acetoxyethyl, N-acetyl-aminoethyl, 3-(2-pyrrolidone)propyl, optionally substituted phenylethyl, phenylpropyl, phenylbutyl, or phenylpentyl.

Groups $R_3$ and $R_4$ taken together may, for example, be —$(CH_2)$—O—$(CH_2)_2$—, —$(CH_2)_5$—, —$C(CH_3)_2SCH_2CH_2CH_2$—, or —$C(CH_3)_2SSCH_2CH_2$—

Group $R_4$ may for example be hydrogen, methyl or ethyl;

Group $R_5$ may for example be hydrogen, or a group $R_{20}C(O)$— where $R_{20}$ is methyl or ethyl;

Group $R_6$ may for example be hydrogen, methyl, ethyl, n- or iso-propyl, n-, sec- or tert-butyl, or a group D-$(CH_2)_m$— as exemplified above for $R_1$ and $R_2$.

Examples of specific compounds according to the invention are those identified in the Examples below.

Compounds according to the present invention in which $R_5$ is hydrogen, and $R_3$ and $R_4$ are other than hydrogen, may be prepared by a process comprising: condensing an acid of formula (II) or an activated derivative thereof with an amine of formula (III)

(II)

$$A\diagdown_B\diagup^X\diagdown_{OH}$$

(III)

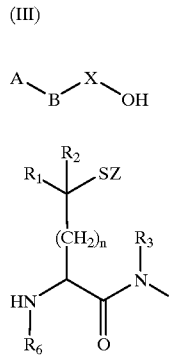

wherein A, B X, n, $R_1$, $R_2$, $R_3$, $R_4$, and $R_6$ are as defined in general formula (I) except that any substituents in A, $R_3$, and $R_4$, which are potentially reactive in the condensation reaction may themselves be protected from such reaction, and Z represents a mercapto protecting group, and subsequently removing the protecting group Z and any protecting groups present in A, $R_3$, and $R_4$.

Active derivatives of acids (II) include activated esters such as the hydroxybenzotriazolyl, hydroxysuccinyl or pentafluorophenyl ester, acid anhydrides and acid halides, eg chlorides. Suitable mercapto protecting groups may be selected from those known in the art and include trityl.

Compounds according to the present invention in which $R_5$ is hydrogen, and $R_3$ and $R_4$ are both hydrogen, may be prepared by a process comprising: condensing an acid of formula (II) or an activated derivative thereof with an amine of formula (IV)

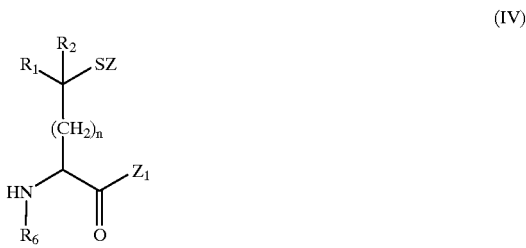

(IV)

wherein n, Z, $R_1$, $R_2$, and $R_6$ are as defined in general formula (I), and $Z_1$ represents a protected amino group, and subsequently removing the protecting group Z and the protecting group(s) present in $Z_1$.

In the foregoing reaction, in addition to the usual protected amino groups used in solution peptide synthesis, the protected amino group $Z_1$ may be an amino group covalently linked to a solid state support such as an amino functionalised resin as used in solid phas e peptide synthesis. In such a case, the free amino compound of the invention is cleaved from the resin by photolysis or acid hydrolysis in the usual way.

Com pounds according to the present invention in which $R_5$ is acyl may be prepared by acylation of a compound of the invention wherein $R_5$ is hydrogen, or by a process comprising analogous to the above wherein the group Z in compounds (III) or (IV) is the desired acyl group $R_5$.

Compounds of formula (I) are useful in human or veterinary medicine since they are active as inhibitors of MMPs Accordingly in another aspect, this invention concerns:

(i) a method of man agement (by which is meant treatment or prophylaxis) of diseases or conditions mediated by MMPs in mammals, in particular in humans, which method comprises administering to the mammal an effective amount of a compound as defined with respect to formula (i) above, or a pharmaceutically acceptable salt thereof; and (ii) a compound as defined with respect to formula (I) for use in human or veterinary medicine, particularly in the management (by which is meant treatment or prophylaxis) of diseases or conditions mediated by MMPs; and (iii) the use of a compound as defined with respect to formula (I) in the preparation of an agent for the management (by which is meant treatment or prophylaxis) of diseases or conditions mediated by MMPs.

Diseases or conditions mediated by MMPs include those involving tissue breakdown, angiogenesis, and inflammation, in particular rheumatoid arthritis, osteoarthritis, periodontitis, gingivitis, corneal ulceration, wound healing, psoriasis, tumour invasion by secondary metastases, tumour growth, proliferative retinopathy, neovascular glaucoma, ocular tumours, angiofibromas and hemangiomas as well as neuroinflammatory disorders, including those involving myelin degradation, for example multiple sclerosis.

In a further aspect of the invention there is provided a pharmaceutical or veterinary composition comprising a compound of formula (I) together with a pharmaceutically or veterinarily acceptable excipient or carrier.

One or more compounds of general formula (I) may be present in the composition together with one or more excipient or carrier.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy. Optimum dose levels and frequency of dosing will be determined by clinical trial.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite os disodium edeate; preservatives including bactericidal and fungicidal agents such as phenyl mercuric acetate or nitrate, benzalkonium chloride or chlorhexidine, and thickening agents such as hypromellose may also be included.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

The following examples illustrate embodiments of the invention. In the examples, the following abbreviations have been used throughout:

| | |
|---|---|
| WSCDI | N-Ethyl-N'-(3-dimethylaminopropyl)carbodiimide hydrochloride |
| HOBt | 1-Hydroxybenzotriazole |
| DMF | Dimethylformamide |
| DCM | Dichloromethane |
| TFA | Trifluoroacetic acid |
| TBTU | O-(Benzotriazol-1-yl)-1,1,3,3-tetramethyluronium tetrafluoroborate |
| HATU | O-(7-Azabenzotriazol-1-yl)-1,1,3,3-tetramethyluronium hexafluorophosphate |
| TLC | Thin layer chromatography |

EXAMPLE 1

Biphenyl-4-carboxylic acid (1R-carbamoyl-2-mercaptoethyl)-amide

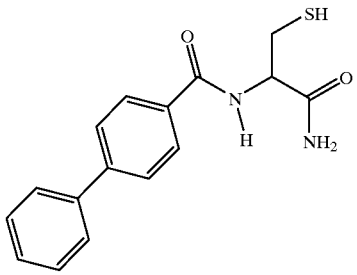

Rink resin (0.25g, 0.13 mmol) with a substitution of 0.52 mmol1g was swollen in 5 ml of dimethylformamide (DMF) in a 20 ml reaction vessel and drained after 30 minutes. A freshly prepared solution of Fmoc-S-trityl-L-cysteine (0.304 g, 0.52 mmol), HOBt (80 mg ) and diisopropyl carbodiimide (82 µL) in DMF (5 ml) was added to the resin and the resulting mixture was then gently shaken for 4 h at room temperature. The resin was then drained, washed with DMF (2×10 ml), dichloromethane (DCM) 3×15 ml, methanol (2×10 ml), DCM (2×10 ml) and then dried in vacuo. The resin gave a negative Kaiser test. A 20% solution of piperidine in DMF (5 ml) was added to the resin. After 5 min this was drained from the resin and replaced with a further 5 ml of piperidine solution and the resin gently agitated for 25 minutes before the solution was drained and the resin washed thoroughly with DMF (5×10 ml). A resin bead gave a positive Kaiser test. A solution of 4-biphenylcarboxylic acid (103 mg, 0.52 mmol), HOBt (80 mg), TBTU (168 mg) and diisopropylethyl amine (163 µL) in DMF (5 ml) was mixed together for 5 minutes and then added to the DMF swelled resin. The resin mixture was gently agitated for 18 h and then drained, washed and dried as described above.

The desired compound was liberated from the resin by treatment for 2 h with a solution (4 ml) of a TFA solution containing anisole (0.2 ml), ethanedithiol (0.3 ml), thioanisole (0.45 ml), water (0.2 ml) and triisopropylsilane (0.15 ml) made upto 10 ml. The TFA solution was then filtered into a collection tube, the resin washed with a further 2 ml of TFA and the combined filtrates evaporated to leave a solid gum. Trituration with cold diethylether (10 ml) caused the desired product to precipitate. The ether was removed by decanting and the solid washed twice more with cold ether before being dried in vacuo to leave 32 mg of the desired product as a white solid, m.p 212 (decomp); $^1$H nmr (MeOD) 2.82 (1H, dd, J=7.5, 13.7 Hz, CH$_a$H$_b$S), 2.93 (1H, dd, J=6.2, 13.7 Hz, CH$_a$H$_b$S), 4.81 (1 H, dd, J=6.2, 7.6 Hz, CHCO), 7.24 (1 H, brt, aromatic), 7.33 (2H, m, Ar), 7.58 (2H, d, J=9.5 Hz, Ar), 7.62 (2H, d, J=9.3 Hz, ArCO) and 7.86 (2H, d, J=9.3 Hz); m/z=301 (M+H).

The following examples were prepared using by methods analogous to those of Example 1:

EXAMPLE 2

Biphenyl-4-carboxylic acid (1S-carbamoyl-2-mercaptoethyl)-amide

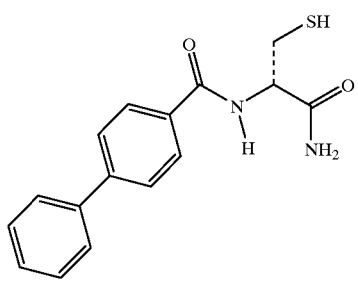

m/z=301 (M+H).

EXAMPLE 3

4'-Chloro-biphenyl-4-carboxylic acid (1R-carbamoyl-2-mercaptoethyl)-amide

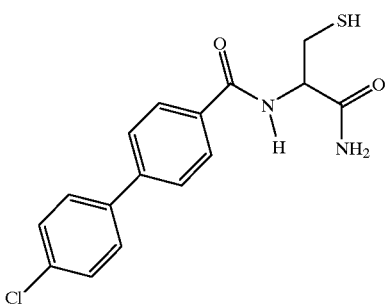

$^1$H nmr (MeOD) 2.82 (1H, dd, J=7.7,13.8 Hz, CH$_a$H$_b$S), 2.91 (1H, dd, J=5.6,13.8 Hz, CH$_a$H$_b$S), 4.61 (1H, m, NCHCO), 7.37 (2H, m, J=8.6 Hz), 7.55 (2H, d, J=8.6 Hz, Ar), 7.62 (2H, d, J=8.6 Hz, ArCO) and 7.86 (2H, d, J=8.6 Hz); m/z=335, 337 (M+H).

EXAMPLE 4

4'-Hexyl-biphenyl-4-carboxylic acid (1R-carbamoyl-2 mercaptoethyl)-amide

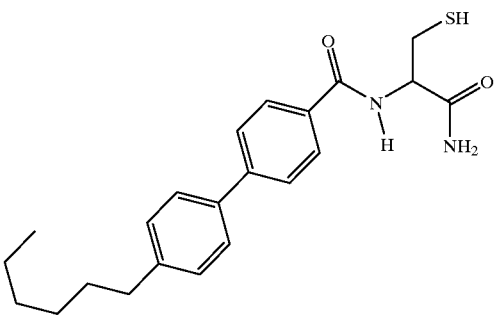

a white solid, $^1$H nmr (MeOD) 0.80 (3H, t, J=7.1 Hz, CH$_3$), 1.23 (6H, m, (CH$_2$)$_3$), 1.55 (2H, m, CH$_2$Me), 2.56 (2H, t, J=7.6 Hz, CH$_2$Ar), 2.83 (1H, dd, J=7.6, 13.9 Hz, CH$_a$H$_b$S), 2.91 (1H, dd, J=5.5, 13.9 Hz, CH$_a$H$_b$S), 4.61 (1H, dd, J=5.4, 7.6 Hz, NCHCO), 7.17 (2H, m, J=8.2 Hz), 7.48 (2H, d, J=8.3 Hz, Ar), 7.63 (2H, d, J=8.6 Hz, ArCO) and 7.85 (2H, d, J=8.6 Hz, ArCO); m/z=385 (M+H).

EXAMPLE 5

Biphenyl-4-carboxylic acid (1R-carbamoyl-2-mercapto-2 methylpropyl )amide

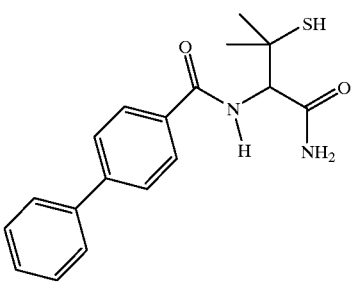

a white solid, $^1$H nmr (CDCl$_3$) 1.41 (3H, s, CH$_3$), 1.66 (3H, s, CH$_3$), 3.66 (2H, brs, NH$_2$), 4.69 (1H, d, J=8.8 Hz, NCHCO), 5.62 (1H, brs, SH), 6.51 (1H, brs, NH), 7.37 (1H, m, aromatic), 7.44 (2H, d, J=6.9 Hz, Ar), 7.62 (2H, d, J=6.8 Hz, Ar), 7.70 (2H, d, J=8.3 Hz, ArCO) and 7.91 (2H, d, J=8.3 Hz, ArCO).

EXAMPLE 6

4'-Octyloxybiphenyl-4-carboxylic acid (1R-carbamoyl-2 mercaptoethyl)amide

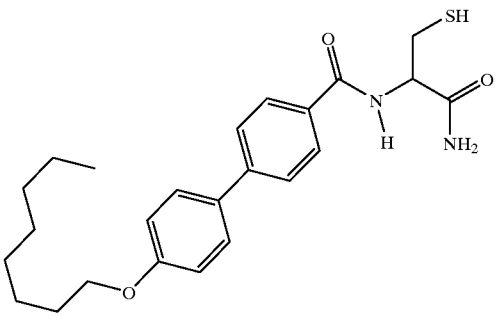

m/z=429 (M+H).

EXAMPLE 7

4'-Ethylbiphenyl-4-carboxylic acid (1R-carbamoyl-2-mercaptoethyl)amide

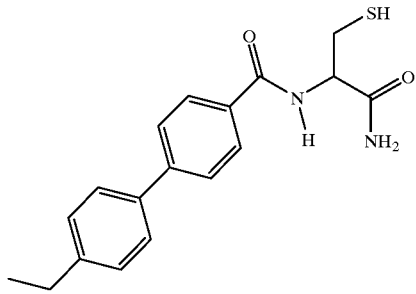

m/z=329(M+H).

EXAMPLE 8

3-Phenylpropynoic acid (1-carbamoyl-2-mercaptoethyl)amide

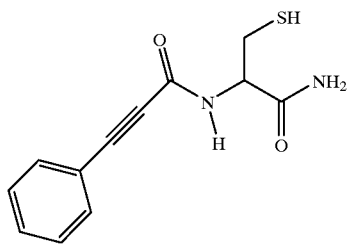

$^1$H nmr (MeOD) 2.71 (1H, dd, J 7.3,13.8 Hz, CH$_a$H$_b$S), 2.82 (1H, dd, J=5.4, 13.9 Hz, CH$_a$H$_b$S), 3.52 (2H, brs, NH$_2$), 4.47 (1H, dd, J=5.5, 7.3 Hz, NCHCO), 7.28 –7.45 (3H, m, aromatic), 7.51 (2H, m, Ar); m/z (M+H).

EXAMPLE 9

2R-(Biphenyl-4-sulfonyamino)-3-mercaptopropionamide

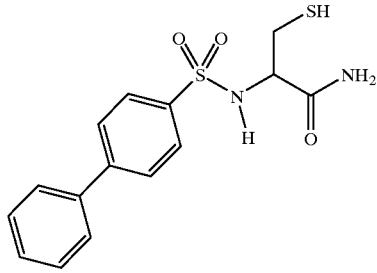

$^1$H nmr (MeOD) 2.7 3 (2, d, J=6.0, 13.6 Hz, CH$_2$S), 3.99 (1H, t, J=6.0 Hz, NCHCO), 7.37 –7.54 (3H, m, Ar), 7.69 (2H, brd, J=6.8 Hz, Ar), 07.83 (2H, d, J=8.6 Hz and 7.94 (2H, d, J=8.5 Hz, ArSO$_2$).

EXAMPLE 10

Biphenyl-4-carboxylic acid (2-mercaptoethyl-1R-methylcarbamoyl)amide

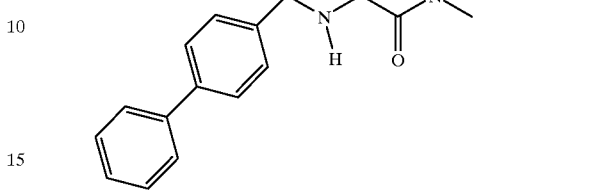

Fmoc-S-trityl-L-cysteine (5.30 g, 9.04 mmol) and HOBt (1.46 g) were dissolved in DMF (60 ml) and cooled in an ice bath. WSCDI (2.08 g, 10.86 mmol) was added and the solution was stirred for 2 h at 0° C. when a solution of methylamine in ethanol (2.25 ml of a 33% solution (8.03M)) was added. The reaction was stirred for 18 h at room temperature and then the solvents were removed in vacuo and the residue dissolved in ethyl acetate (70 ml) and washed successively with 1M HCl, 1M sodium carbonate solution, brine, dried (MgSO$_4$) and filtered. The solvent was removed to leave a sticky foam which was purified by column chromatography (silica gel) in 0–5% methanol in DCM to give the methyl amide as a white foam (2.83g, 52%). The amide was dissolved in 20% piperidine in DMF (25 ml) and stirred for 1 h before the solvent was removed in vacuo and the residue purified by column chromatography (silica gel) to give the free amine as an oil. The amine (0.90 g, 2.39 mmol), 4-biphenylcarboxylic acid (0.57 g, 2.87 mmol) and HATU (1.09 g, 2.87 mmol) were dissolved in DMF (50 ml). The solution was cooled to 0° C. and diisopropylethylamine (0.99 ml, 5.73 mmol) was added and the solution stirred for 4 h at room temperature. The solvents were removed and the residue dissolved in ethyl acetate and washed with 1M HCl, 1M sodium carbonate solution, brine and dried (MgSO$_4$). The solution was filtered and the solvent removed in vacuo to give the tritylated product as an essentially pure white foam. A cooled solution (10 ml) of TFA (2%) and triisopropylsilane (5%) was added to the foam and the resulting mixture was then stirred at room temperature for 1 h when tlc indicated that the reaction was complete. The solvent was removed to leave a white solid which was washed (×3) with ice cold diethyl ether to leave the desired substituted thiol as an amorphous white solid. $^1$H nmr (d$^6$-DMSO) 2.39 (1H, dd, J=8.6, 8.4 Hz, SH), 2.61 (3H, d, J=4.5 Hz, NMe), 2.82–3.05 (2H, m, CH2S), 3.98 (1H, brm, NH), 4.52 (1H, m, NCHCO), 7.41 (1H, m, aromatic), 7.48 (2H, d, J=7.5 Hz), 7.74 (2H, d, J=7.4 Hz), 7.79 (2H, d, J=8.3 Hz), ArCO), 8.04 (2H, d, J=8.4 Hz, ArCO) and 8.58 (1H, d, J=8.0 Hz, NH); m/z 315 (M+H).

The following example was prepared using a method analogous to that of Example 10:

EXAMPLE 11
Biphenyl-4-carboxylic acid (1R-dimethylcarbamoyl-2-mercaptoethyl)-amide

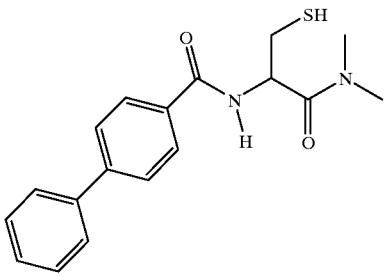

$^1$H nmr (MeOD) 2.72 (1h, dd, J=6.9, 13.6 Hz, CH$_a$H$_b$S), 2.90 (3h, s, NMe), 2.90 (1h, m, CH$_a$H$_b$S), 3.14 (3h, s, NMe), 5.07 (1h, t, J=7.0 Hz, NCHCO), 7.35 (1h, m, AR), 7.35 (2h, d, J=7.5 Hz), 7.56 (2h, d, J=7.6 Hz), 7.62 (2h, d, J=8.5 Hz, ArCO) and 7.82 (2h, d, J=8.5 Hz, ArCO); m/z 329 (m+h).

What is claimed is:

1. A compound of formula (I)

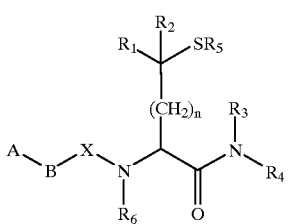

wherein:

n is 0 or 1;

A represents an optionally substituted phenyl or pyridryl group;

B represents a divalent 1,4-phenylene moiety or a divalent $C_1$–$C_4$ alkylene or $C_2$–$C_4$ alkenylene or $C_2$–$C_4$ alkynylene moiety;

X represents —C(=O)— or —S(=O)$_2$—, $R_1$ and $R_2$
  (i) independently represent
    hydrogen,
    a $C_1$–$C_6$ alkyl group, or
    a group D-($C_1$–$C_6$ alkyl)- wherein D represents
      a 5- or 6-membered N-heterocyclic ring which (a) is attached via the N atom, (b) optionally contains N, O and/or S, SO or SO$_2$ as an additional ring member, (c) is substituted by oxo on one or both C atoms adjacent to the linking N atom and (d) is optionally benz-fused or optionally substituted on one or more other C atoms by $C_1$–$C_6$alkyl, or oxo and/or on any additional N atoms by $C_1$–$C_6$ alkyl, phenyl or heteroaryl; or
  (ii) taken together with the carbon atom to which they are attached form a cycloalkyl or cycloalkenyl ring;

$R_3$ represents:
  (a) an optionally substituted cycloalkyl or cycloalkenyl ring or
  (b) a group —CHR$^x$R$^y$ wherein (i) R$^x$ and R$^y$ each independently represents an optionally substituted phenyl or heteroaryl group which may be linked covalently to each other by a bond or by a divalent $C_1$–$C_4$ alkyl or $C_1$–$C_4$ alkenyl bridge, or (ii) R$^x$ represents a group D-($C_1$–$C_6$ alkyl)- wherein D is as defined above in relation to $R_1$ and $R_2$, or is an optionally substituted phenyl or heteroaryl, group, and R$^y$ represents an optionally substituted phenyl or heteroaryl ring;
  (c) a group of formula -(Z'—O)$_w$-Z wherein Z' is straight or branched $C_1$–$C_6$ alkyl optionally interrupted by one or more non-adjacent S and/or N atoms, w is an integer >1, and no continuous linear sequence of atoms in the group $R_4$ is >12, or
  (d) hydrogen, $C_1$–$C_6$ alkyl, $C_1$–$C_4$ perfluoroalkyl, or a group D-($C_1$–$C_6$ alkyl)- wherein D is as defined above in relation to $R_1$ and $R_2$, or is hydroxy, $C_1$–$C_6$ alkoxy, $C_1$–$C_6$ alkylthio, acylamino, optionally substituted phenyl or heteroaryl, NH$_2$, or mono- or di-($C_1$–$C_6$ alkyl)amino;
  or $R_3$ and $R_4$ taken together represent a divalent chain of formula -C(R$^a$)(R$^b$)-A$^1$-Alk- wherein R$^a$ and R$^b$ are independently hydrogen or $C_1$–$C_6$ alkyl, A$^1$ is a bond, —O—, —S—, —S—S—, —NH— or —NR$^a$— wherein R$^a$ is $C_1$–$C_6$ alkyl, and Alk is a divalent $C_1$–$C_4$ alkylene moiety;

$R_4$ represents hydrogen or a $C_1$–$C_6$ alkyl group;

$R_5$ represents hydrogen or acyl; and $R_6$ represents hydrogen, a $C_1$–$C_6$ alkyl group, or a group D-($C_1$–$C_6$ alkyl)- wherein wherein D is as defined above in relation to $R_1$ and $R_2$;

or a pharmaceutically acceptable salt, hydrate or solvate thereof.

2. A compound as claimed in claim 1 wherein A is phenyl, 4-chlorophenyl, 4-ethylphenyl, 4-n-hexylphenyl, 4-n-octyloxyphenyl; or pyridin-4-yl.

3. A compound as claimed in claim 1 or claim 2 wherein B is 1,4-phenylene, —CH$_2$—, —CH$_2$CH$_2$—, —CH$_2$CH$_2$CH$_2$—, —CH$_2$(CH$_2$)$_2$CH$_2$—, —CH=CH$_2$—, —CH=CH$_2$CH$_2$—, —CH$_2$CH=CH$_2$—, —C≡C—, —CH$_2$C≡CCH$_2$—, —CH$_2$C≡C—, or —C≡CCH$_2$—.

4. A compound as claimed in claim 1 wherein $R_1$ and $R_2$ are independently hydrogen; methyl, ethyl, n- or iso-propyl, n-, sec- or tert-butyl, n-pentyl or n-hexyl; or a group D-(CH$_2$)$_m$—, wherein m is 1, 2, 3 or 4, and D is maleimido, succinimido, phthalimido, 1,2-dimethyl-3,5-dioxo-1,2,4-triazolidin-4-yl, 3,4,4-trimethyl-2,5-dioxo-1-imidazolidinyl, 2-methyl-3,5-dioxo-1,2,4-oxadiazol-4-yl, 3-methyl-2,4,5-trioxo-1-imidazolidinyl, 2,5-dioxo-3-phenyl-1-imidazolidinyl-2-oxo-1-pyrrolidinyl, 2,5-dioxo-1-pyrrolidinyl, 2,6-dioxopiperidinylnaphththalimido (ie 1,3-dihydro-1,3-dioxo-2H-benz[f]isoindol-2-yl), 1,3-dihydro-1-oxo-2H-benz[f]isoindol-2-yl, 1,3-dihydro-1,3-dioxo-2H-pyrrolo[3,4-b]quinolin-2-yl, 2,3-dihydro-1,3-dioxo-1H-benz[d,e]isoquinolin-2-yl group, or saccharinyl (1,1,3-trioxo-benz[3,4-d]isothiazol-2-yl).

5. A compound as claimed in claim 1 to wherein, taken together with the carbon atom to which they are attached, groups $R_1$ and $R_2$ form a cyclopropyl, cyclobutyl cyclopentyl, cyclohexyl, cyclohex-1,2-enyl, cyclohex-2,3-enyl, or cyclohex-3,4-enyl ring.

6. A compound as claimed in claim 1 wherein $R_3$ is:
cyclopropyl, cyclobutyl, cyclopentyl, cycichexyl cycloheptyl or cyclooctyl; or
phenyl, 2-methoxyphenyl, 3-methoxyphenyl, 4-methoxyphenyl, 3,4-dimethoxyphenyl, 2-fluorophenyl, 3-fluorophenyl, 4-fluorophenyl, 2-chlorophenyl, 3-chlorophenyl, 4-chlorophenyl, 3,4-dichlorophenyl, 3,5-dichlorophenyl, 2-bromophenyl, 3-bromophenyl, 4-bromophenyl, 2-iodophenyl, 3-iodophenyl, 4-iodophenyl, 2-methylphenyl, 3-methylphenyl, 4-methylphenyl, 3,4-dimethyl, 2-t-butylphenyl, 3-t-butylphenyl, 4-t-butylphenyl, 4-t-butyl-2,6-dimethylphenyl, 2-nitrophenyl, 3-nitrophenyl, 4-nitrophenyl, 2-cyanophenyl, 3-cyanophenyl, 4-cyanophenyl, 2-acetylphenyl, 3-acetylphenyl, 4-acetylphenyl, 2-methylsulphonylphenyl, 3-methylsulphonylphenyl, 4-methylsulphonylphenyl, 2-trifluoromethylphenyl, 3-trifluoromethylphenyl, 4-trifluoromethylphenyl, 3,5-ditrifluoro-methylphenyl, 2-aminophenyl, 3-aminophenyl, 4-aminophenyl, 2-N,N-dimethylaminophenyl, 3-N,N-dimethylaminophenyl, 4-N,N-dimethylaminophenyl, 2-hydroxyphenyl, 3-hydroxyphenyl, 4-hydroxyphenyl, 2-napthyl, furan-2-yl, thien-2-yl, pyrrol-2-yl, tetrahydrofuran-2-yl, imidazol-2-yl, thiazol-2-yl, 4-ethoxycarbonyl-methylthiazol-2-yl, 4-phenylthiazol-2-yl, 4,5-dimethylthiazol-2-yl, 5-bromothiazol-2-yl, 4-tert-butylthiazol-2-yl, benzothiazol-2-yl, 1,2,4-oxadiazol-5-yl, 3-methyl-1,2,4-oxadiazol-5-yl , 3-phenyl-1,2,4-oxadiazol-5-yl, 1,2,4-oxadiazol-3-yl, 1,3,4-oxadiazol-2-yl, 1,2,4-thiadiazol-5-yl, 3-phenyl-1,2,4-thiadiazol-5-yl, 1,3,4-thiadiazol-2-yl, 5-methyl-1,3,4-thiadiazol-2-yl, pyridin-2-yl, pyridin-3-yl, pyridin-4-yl, N-oxides of pyridin-2-yl pyridin-3-yl and pyridin-4-yl, piperazin-1-yl, indol-2-yl, benzimidazol-2-yl, benzotriazol-2-yl, pyrazin-2-yl, 1,2-pyridazin-3-yl, 1,3-pyrimidin-5-yl, 1,3-dithian-2-yl, benzo[b]thien-2-yl, isoxazol-5-yl, or quinolin-3-yl; or a group —CHR$^x$R$^y$ wherein R$^x$ and R$^y$ independently represent phenyl, 4-chlorophenyl or pyridinyl; or 2-(2-methoxyethoxymethoxy)ethyl, 1,1-dimethyl-2-(2-methoxyethoxymethoxy)ethyl, 2-(2-ethoxyethoxymethoxy)ethyl, 2-(2-(2-methoxyethoxy)ethoxy)ethyl, 2-(2-(3-methoxypropoxymethoxy)ethyl, 3-(2-methoxyethoxymethoxy)propyl, 2,2-dimethyl-3-(2-methoxyethoxymethoxy)propyl, 2-(2-methoxyethoxy)ethyl, or 3-(2-methoxyethoxy)-propyl; or hydrogen, methyl, ethyl, n- or iso-propyl, n-, sec- or tert-butyl, a group D-(CH$_2$)$_m$— wherein D and m are as defined in claim 5, hydroxyethyl, hydroxypropyl, 2,2-dimethyl-3-hydroxypropyl, hydroxybutyl, methoxyethyl, ethoxyethyl, methoxypropyl, 2,2-dimethyl-3-methoxypropyl, 2,2-dimethyl-3-ethoxypropyl, 2-ethylthioethyl, 2-acetoxyethyl, N-acetyl-aminoethyl, 3-(2-pyrrolidone)propyl, optionally substituted phenylethyl, phenylpropyl, phenylbutyl, or phenylpentyl.

7. A compound as claimed in claim 1 to wherein R$_3$ and R$_4$ taken together represent —(CH$_2$)—O—(CH$_2$)$_2$—, —(CH$_2$)$_5$—, —C(CH$_3$)$_2$SCH$_2$CH$_2$CH$_2$—, or —C(CH$_3$)$_2$SSCH$_2$CH$_2$—.

8. A compound as claimed in claim 1 wherein R$_4$ is hydrogen, methyl or ethyl.

9. A compound as claimed in claim 1 wherein R$_5$ is hydrogen, or a group R$_{20}$C(O)— where R$_{20}$ is methyl or ethyl.

10. A compound as claimed in claim 1 wherein R$_6$ is hydrogen, methyl, ethyl, n- or iso-propyl, n-, sec- or tert-butyl, or a group D-(CH$_2$)$_m$— wherein D and m are as defined in claim 5.

11. A pharmaceutical composition comprising a compound as claimed in claim 1 together with a pharmaceutically acceptable carrier.

* * * * *

UNITED STATES PATENT AND TRADEMARK OFFICE
CERTIFICATE OF CORRECTION

PATENT NO. : 6,258,851 B1  Page 1 of 1
DATED : July 10, 2001
INVENTOR(S) : Christopher David Floyd et al.

It is certified that error appears in the above-identified patent and that said Letters Patent is hereby corrected as shown below:

Column 15,
Line 39, "pyridryl" has been replaced with -- pyridinyl --.

Column 16,
Line 57, "to" has been deleted.
Line 64, "cycichexyl" has been replaced with -- cyclohexyl --.

Column 18,
Line 19, "to" has been deleted.

Signed and Sealed this

Third Day of June, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,258,851 B1
DATED : July 10, 2001
INVENTOR(S) : Christopher David Floyd et al.

It is certified that error appears in the above-identified patent and that said Letters Patent is hereby corrected as shown below:

Column 16,
Line 2, "$C_1$–$C_4$ alkenyl bridge" has been replaced with -- $C_2$–$C_4$ alkenyl bridge --.

Signed and Sealed this

Twelfth Day of August, 2003

JAMES E. ROGAN
*Director of the United States Patent and Trademark Office*